United States Patent
Saito et al.

(10) Patent No.: US 10,294,519 B2
(45) Date of Patent: May 21, 2019

(54) METHOD AND APPARATUS FOR NUCLEIC ACID ANALYSIS

(75) Inventors: Toshiro Saito, Tokyo (JP); Koshin Hamasaki, Tokyo (JP); Satoshi Takahashi, Tokyo (JP); Muneo Maeshima, Tokyo (JP); Kyoko Imai, Tokyo (JP); Kazumichi Imai, Tokyo (JP); Ryuji Tao, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 869 days.

(21) Appl. No.: 14/233,256

(22) PCT Filed: May 16, 2012

(86) PCT No.: PCT/JP2012/003176
§ 371 (c)(1),
(2), (4) Date: Jan. 16, 2014

(87) PCT Pub. No.: WO2013/011611
PCT Pub. Date: Jan. 24, 2013

(65) Prior Publication Data
US 2014/0200162 A1   Jul. 17, 2014

(30) Foreign Application Priority Data
Jul. 19, 2011   (JP) .................. 2011-157399

(51) Int. Cl.
*C12Q 1/6834*   (2018.01)
*C12N 15/10*    (2006.01)

(52) U.S. Cl.
CPC ....... *C12Q 1/6834* (2013.01); *C12N 15/1065* (2013.01)

(58) Field of Classification Search
None
See application file for complete search history.

(56) References Cited

U.S. PATENT DOCUMENTS

| | | | |
|---|---|---|---|
| 2003/0157504 A1* | 8/2003 | Chee | B01J 19/0046 435/6.11 |
| 2005/0009199 A1 | 1/2005 | Nishida | |
| 2005/0191687 A1* | 9/2005 | Wang | C12Q 1/682 435/6.11 |
| 2007/0099225 A1* | 5/2007 | Wilson | C12N 15/1013 435/6.12 |
| 2010/0009862 A1 | 1/2010 | Nakahara et al. | |

FOREIGN PATENT DOCUMENTS

| | | |
|---|---|---|
| JP | 2005-030950 A | 2/2005 |
| JP | 2008-190937 A | 8/2008 |
| JP | 2008-198937 A | 8/2008 |

OTHER PUBLICATIONS

Das et al (2010 Nucleic Acids Research col. 38 No. 18 e177; published on-line Aug. 10, 2010).*
Klamp et al (Proc. of SPIE vol. 7905 pp. 7905N-1 to 7905N-7) (Year: 2011).*
Chinese Office Action received in corresponding Chinese Application No. 201280034897 dated Sep. 3, 2014.
Schena et al., "Quantitative Monitoring of Gene Expression Patterns with a Complementary DNA Microarray", Science, Oct. 20, 1995, pp. 467-470, vol. 270.
Nakayama et al., " Quantification of mRNA by non-radioactive RT-PCR and CCD imaging system", Nucleic Acids Research, 1992, p. 4939, vol. 20, No. 18.
Valouev et al., "A high-resolution, nucleosome position map of C. elegans reveals a lack of universal sequence-dictated positioning", Genome Research, 2008, pp. 1051-1063, vol. 18.
Linsen et al., "Limitations and possibilities of small RNA digital gene expression profiling", Nature Methods, Jul. 2009, pp. 474-476, vol. 6, No. 7.
Baker, "MicroRNA profiling: separating signal from noise", Nature Methods, Sep. 2010, pp. 687-692, vol. 7, No. 9.
Gazouli et al., "Specific Detection of Unamplified Mycobacterial DNA by Use of Fluorescent Semiconductor Quantum Dots and Magnetic Beads", Journal of Clinical Mirobiology, Aug. 2010, pp. 2830-2835, vol. 48, No. 8.
Rousserie et al., "Semiconductor quantum dots for multiplexed bio-detection on solid-state microarrays", Critical Reviews in Oncology/Hematology, 2010, pp. 1-15, vol. 74.
Repsilber et al., "Two-color Microarray Experiments", Methods of Information in Medicine, 2005, pp. 400-404, vol. 44, No. 3.

* cited by examiner

*Primary Examiner* — Christopher M Gross
(74) *Attorney, Agent, or Firm* — Mattingly & Malur, PC (57) ABSTRACT

A convenient method for nucleic acid analysis is provided, which enables 1000 or more types of nucleic acid to be analyzed collectively with high comprehensiveness and with a dynamic range of at least four digits. In particular, provided is a very effective analytical method especially for untranslated RNAs and microRNAs, of which the types of target nucleic acids is 10000 or lower. Nucleic acids can be analyzed conveniently and rapidly with high comprehensiveness and quantitative performance at single-molecule sensitivity and resolution by following the steps of: preparing a group of target nucleic acid fragments one molecule at a time and hybridizing the nucleic acid molecules, which have known base sequences and have been labeled with the fluorescence substances, with the group of the target nucleic acid fragments to detect the fluorescence substances labeling the hybridized nucleic acid molecules.

3 Claims, 7 Drawing Sheets

F I G . 7

METHOD AND APPARATUS FOR NUCLEIC ACID ANALYSIS

TECHNICAL FIELD

The present invention relates to a method and an apparatus for nucleic acid analysis.

BACKGROUND ART

In recent years, methods for easy analysis of the types and concentrations of nucleic acids contained in samples have been developed. For instance, as disclosed in the Patent Literature 1, for a DNA microarray, many types of synthesized DNAs having sequences capable of identifying known gene sequences are fixed on a support substrate at given positions, nucleic acid samples labelled with a fluorescence substance or the reverse transcription products or the amplified products of the nucleic acid samples are hybridized on the support substrate, and then fluorescence images are captured using a fluorescence scanner, which enables the analysis to determine which gene expresses at how concentration level based on the fluorescence intensity. Moreover, as disclosed in the Non-patent Literature 2, a quantitative PCR method as one of the nucleic acid analytical methods, in which PCR, that is nucleic acid amplification reaction, is used to draw an amplification curve in order to compare the reaction times necessary to produce a given amount of amplification products among the samples. In addition, as disclosed in the Non-patent Literature 3, practically used is the next-generation sequencing method, what is called, for high parallel-performance base sequence analysis, which involves the steps of: inducing PCR in an emersion containing particles; fixing a plurality of particles with the amplification products on a support substrate to cause DNAs to elongate; and incorporating nucleotides labelled with fluorescence substances for fluorescence observation.

CITATION LIST

Non-Patent Literatures

Non-patent Literature 1: Science 1995, Vol. 270, p. 467-470.
Non-patent Literature 2: Nucleic Acid Research, 1992, Vol. 20, pp. 4939.
Non-patent Literature 3: Genome Research 2008, Vol. 18, pp. 1051-1063.
Non-patent Literature 4: Nature Methods, 2009, Vol. 6, pp. 474-476.
Non-patent Literature 5: Nature Methods 2010, Vol. 7, pp. 687-692.

SUMMARY OF INVENTION

Technical Problem

To search for disease-related genes, methods, which involve the step of comparing between the nucleic acid samples from healthy subjects and those from subjects with a specific disease (hereinafter, simply referred to as patients) to search for genes with significantly high or low expression level in the patients, are today's common practice. The most generally used one among these methods involves the steps of selecting candidate genes with different expression levels on a microarray and performing the quantitative PCR on the candidate genes to verify rigorously any difference in expression level. The microarray is characterized in that with higher global identification performance, it has an advantage that is capable of searching more than several tens of thousands for collective analysis and a disadvantage that its quantitative performance is low with 2- to 3.5-digit dynamic range, whereas the quantitative PCR method is characterized in that having high quantitative performance with 6- to 7-digit dynamic range, it has an advantage that it has high quantitative performance and a disadvantage that it is capable of collectively analyzing less number of genes, about 400, leading to lower global identification performance; the above two advantages have been incorporated in this method. For this reason, the method has a persistent problem that to conduct comparative analysis of expression level between samples, two-step experiments, by the microarray method and the quantitative PCR method is unavoidable. In contrast, the next-generation sequencer, which is capable of analyzing collectively a plurality of nucleic acid fragments ranging from hundreds of millions to billions fragments, enables the expression level to be determined by counting nucleic acid fragments in single sequences, indicating that its dynamic range is 8 or more digits. It is suitable for comprehensive expression analysis of 20 thousand or more types of messenger RNAs; however, it is beyond its specification to analysis the expression levels of the nucleic acids, which contain 2,000 or less types of untranslated RNAs and less than several tens of bases, causing problems of high running costs, including the cost of reagents, necessary for single analysis and the long analysis time requiring several tens of hours.

Moreover, as disclosed in the Non-patent Literature 4, the quantitative PCR method or the method using the next-generation sequencer for expression analysis involve PCR amplification of nucleic acid samples; however, since the amplification efficiency depends on base sequences, e.g., their GC content, the nucleic acids of all the samples are not always amplified at the same amplification efficiency, leading to biased nucleic acid population. This causes a problem that the distribution of the abundance of individual nucleic acid molecules is not correctly understood.

The object of the present invention is to provide a convenient nucleic acid analytical method, which is characterized in that with no use of amplification reactions, such as PCR, it exhibits high global identification performance, enabling several thousand or more types of nucleic acids to be collectively analyzed, and high quantitative performance with four-or-more-digit dynamic range. In particular, the object of the present invention is to provide an analytical method highly effective in analyzing untranslated RNAs and microRNAs, which contains ten thousand or less types of target nucleic acids.

Solution to Problem

The present invention relates to a method for analyzing the types and expression levels of nucleic acid molecules at single-molecule sensitivity and resolution by following the steps of: fixing the nucleic acid molecules of samples at the positions spatially separated from each other one at a time; hybridizing the nucleic acids, which have known base sequences and have been labeled with a fluorescence substance, with a group of the nucleic acid molecules of the samples to capture fluorescent images.

Advantageous Effects of Invention

The present invention allows convenient and rapid nucleic acid analysis to be performed at single-molecule sensitivity and resolution with no use of amplification reactions, such as PCR, while ensuring its global identification performance and quantitative performance of the types and abundances of the target nucleic acids.

Moreover, the method of the present invention is applicable to analysis of nucleic acids, as well as analysis of biomolecules, such as proteins, other than nucleic acid samples using an antibody as a capture molecule. For the biomolecule sample composed of more than one type of biomolecule, the biomolecule samples may be analyzed in the same manner as that of the nucleic acid samples, by following the steps of: fixing the target biomolecules at their corresponding fixing positions on the support substrate one at a time while maintaining the regularity; inducing reaction of the target biomolecules for detection, of which property of adsorption to specific biomolecules is known, with the biomolecular samples fixed on the support substrate to detect the target biomolecules. For this reason, the method of the present invention allows convenient and rapid analysis of the biomolecular samples to be performed at single-sensitivity and resolution while ensuring its global identification performance and quantitative performance of the types and abundances of the target biomolecules.

DESCRIPTION OF EMBODIMENTS

In embodiments, disclosed is the method for nucleic acid analysis, which is characterized in that it involves the steps of: preparing a group of target nucleic acid fragments; hybridizing the nucleic acid molecules, which have known base sequences and have been labelled with a group of the target nucleic acid fragments to detect the fluorescence substances labelling nucleic acid molecules; and counting the number of the fluorescence substances.

Moreover, in the embodiments, disclosed is the method for nucleic acid analysis, which is characterized in that it involves the steps of: preparing a group of the target nucleic acid fragments for each molecule; and hybridizing the nucleic acid molecules, which have known base sequences and have been labeled with a fluorescence substance with the group of target nucleic acid fragments to detect the fluorescence substance labeling the hybridized nucleic acid molecules.

Furthermore, in the embodiments, disclosed is the method for nucleic acid analysis, which is characterized in that it involves the steps of: fixing a group of the target nucleic acid molecules one molecule at a time at the positions spatially separated from each other; hybridizing the nucleic acid molecules, which have known base sequences and have been labeled with the fluorescence substance, with the group of the target nucleic acid molecules; and after the hybridization step, measuring the fluorescence of the fluorescence substance.

Additionally, in the embodiments, disclosed is the method for nucleic acid analysis, which is characterized in that it involves the steps of: fixing the group of the target nucleic acid molecules at their corresponding positions on the support substrate one at a time; hybridizing the nucleic acid molecules, which have known base sequences and have been labeled with the fluorescence substance, with the group of the target nucleic acid molecules; and after the hybridization step, measuring the fluorescence of the fluorescence substance.

Moreover, in the embodiments, disclosed is the method for nucleic acid analysis, which is characterized in that it has the steps of: fixing the group of the target nucleic acid fragments on each of particles one molecule at a time; hybridizing the nucleic acid molecules, which have known base sequences and have been labeled with the fluorescence substance, with the nucleic acid molecules on the particles; and after the hybridization step, fixing the particles on the support substrate; and measuring the fluorescence of the fluorescence substance.

Furthermore, in the embodiments, disclosed is the method for nucleic acid analysis, which is characterized in that a group of target nucleic acid fragments are out of minute recipients separated for each nucleic acid sample and all the groups of nucleic acid fragments are hybridized through reaction with the same solution containing the nucleic acid molecules, which have known base sequences and have been labeled with the fluorescence substance.

Additionally, in the embodiments, disclosed is the method for nucleic acid analysis, which is characterized in that the fluorescence substances are particles containing a plurality of types of fluorescence substances with different compounding ratios.

Moreover, in the embodiment, disclosed is the method for nucleic acid analysis, which is characterized in that it involves the steps of counting the number of fluorescence luminescent spots for each of the types of the nucleic acid molecules using the labeling, with the same fluorescence substance, of the types of nucleic acids other than given types of nucleic acids; and calculating the ratio of the number of luminescent spots for each of the given types of nucleic acids to the total number of the luminescent spots to evaluate the abundance for each of the given types of nucleic acids.

Furthermore, in the embodiments, disclosed is the method for nucleic acid analysis, which is characterized in that it involves the steps of: labeling a group of the target nucleic acid fragments with a common fluorescence substance; hybridizing the nucleic acid molecules, which have known base sequences labeled with fluorescence substances different from the aforementioned fluorescence substance; and calculating the ratio of the number of the luminescent spots of the former luminescence substance to that of the latter luminescence substance to evaluate the abundance of for each type of the target nucleic acid fragments.

Additionally, in the embodiments, disclosed is the method for nucleic acid analysis, which is characterized in that it involves the steps of: preparing the particles, on which the group of the target nucleic acid fragments one molecule at a time; and hybridizing the nucleic acid molecules, which have known base sequences and have been labels with the fluorescence substance, with the group of the target nucleic acid fragments to detect the fluorescence substances labeling the nucleic acid molecules.

Moreover, in the embodiments, disclosed is the method for nucleic acid analysis, which is characterized in that the particles, on which the group of the target nucleic acid fragments are fixed one molecule at a time, are magnetic particles; the fluorescence substance labels are the particles containing a plurality of types of fluorescence substances with different compounding ratios; and after hybridization, the nucleic acid molecules labeled with the fluorescence substances, which have not been hybridized, are separated from the magnetic particles to detect the fluorescence substances labeling the nucleic acid molecules hybridized with the nucleic acid molecules on the magnetic particles.

Furthermore, in the embodiments, disclosed is the method for nucleic acid analysis, which is characterized in that it involves the steps of: counting the number of luminescent spots of fluorescence for each of the nucleic acid molecules using the labeling, with the same fluorescence substance, of nucleic acids other than given types of nucleic acids; and calculating the ratio of the number of luminescent spots for each of given types of nucleic acids to the total number of luminescent spots to evaluate the abundance of each of the give types of nucleic acids.

Additionally, in the embodiments, disclosed is the method for nucleic acid analysis, which is characterized in that it involves the steps of: labeling the group of the target nucleic acid molecules with the same fluorescence substance; hybridizing the nucleic acid molecules, which have known base sequences and have been labeled with a fluorescence substance different from the aforementioned fluorescence substances; and calculating the ratio of the former number of the luminescent spots to the latter number of luminescent spots to evaluate the abundance for each of the types of the target nucleic acids.

Moreover, in the embodiments, disclosed is an apparatus for nucleic acid analysis, which is characterized in that it has a part for fixing the group of the target nucleic acid molecules at their corresponding positions spatially separated from each other one molecule at a time; a part for hybridizing the nucleic acid molecules, which have known base sequences and have been labeled with fluorescence substances, with the group of the target nucleic acid molecules; and a part for, after the hybridization step, measuring the fluorescence of the fluorescence substances.

Hereinafter, the aforementioned and other novel features and effects of the present invention are described by reference to accompanying drawings. Herein, certain embodiments are described in detail only for full understanding of the present invention but not limited to the aforementioned descriptions.

First Embodiment

Figure 1:
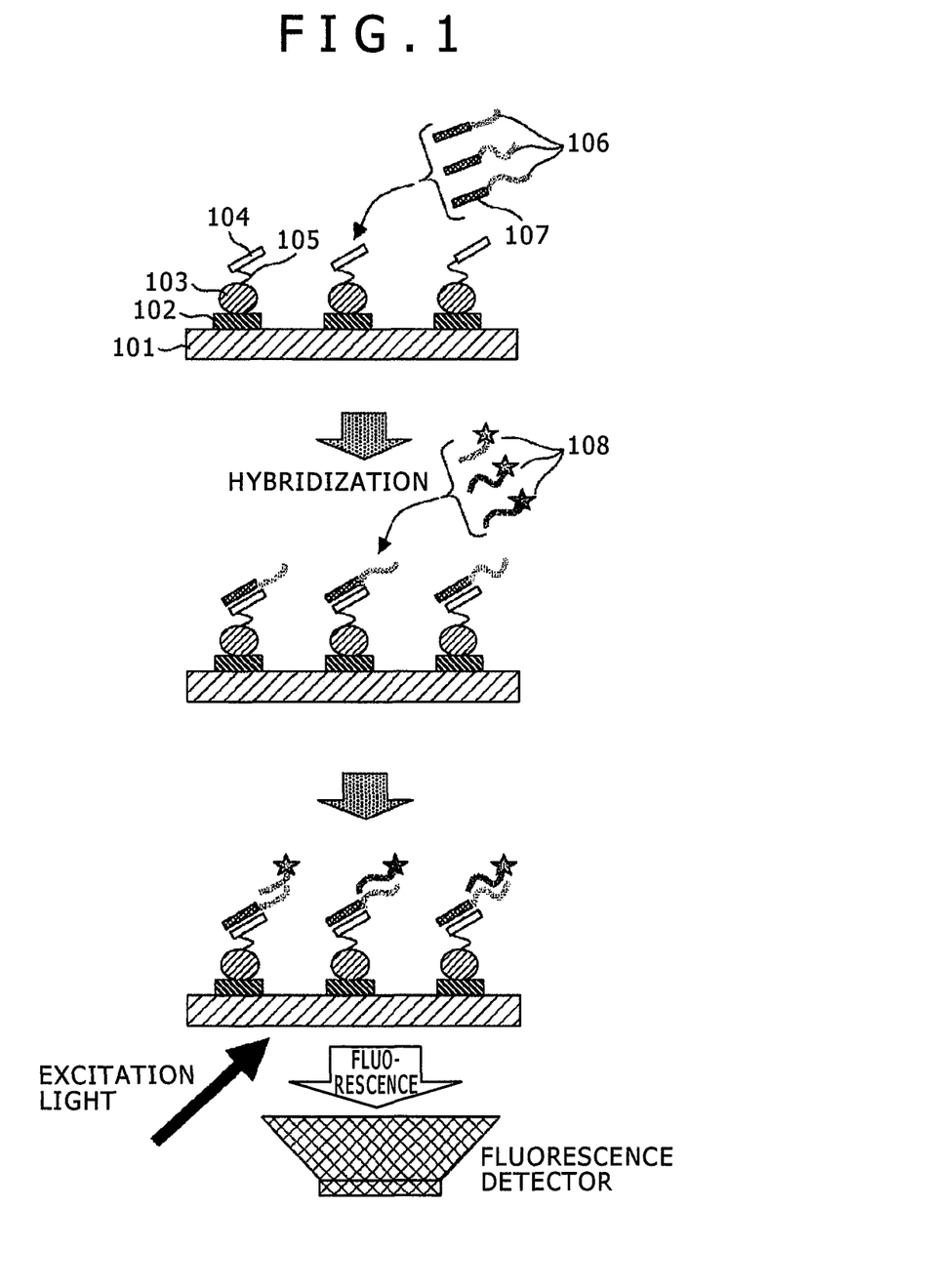
FIG. 1 is a view explaining an example of an analysis method according to this embodiment.

The configuration and analytical method of a device according to the first embodiment is described by reference to FIG. 1.

The configuration of the device according to the first embodiment is as described below. On a support substrate 101, bond pads 102 are formed. A glass (e.g., quartz) substrate and a silicon wafer may be used for the support substrate 101. Any of materials, such as metals and metallic oxides, different from that for the support substrate 101 may be used for the bond pads 102. The method for forming the bond pads is described in a third embodiment in detail. The bond pads 102 are preferably formed on the support substrate 101 with regularity, of which detail is described in the third embodiment. On the bond pads 102, particles 103 are fixed. Only one particle is fixed on each of bond pads. On the particles 103, only one capture molecule 104 is fixed through a binding molecule 105. Depending on the types of target nucleic acid fragments 106, a various combination of molecule groups may be used for a capture tag molecules 107, capture molecules 104, and binding molecules 105. For example, if the target nucleic acid fragments 106 are RNA reverse transcription products, primer DNAs may be used for the capture tag molecules 107 during reverse transcription reaction; thereby, the nucleic acid molecules having the complementary sequences to the capture, tag molecules 107 may be used for the capture molecules 104. Alternatively, the nucleic acid molecules with biotin at the ends thereof may be used for the capture tag molecules 107 and the molecules with avidin at the ends thereof may be used for the capture molecules 104. Alkane molecules, each containing less than about ten carbon atoms, which bind to the capture molecules 104 through chemical bond and have biotin at another ends thereof may be used for the binding molecules 105. In this case, it is preferable that the surfaces of the particles 103 have been modified with avidin, streptavidin, or the like. If the capture tag molecules 107 and the capture molecules 104 are the nucleic acid molecules having complementary sequences to each other, it is preferable to hybridize between both the molecules to induce reaction between them. Alternatively, it is preferable to link both the molecules by means of chemical bond through ligation. As a result, on the support substrate 101, the target nucleic acid fragments 106 would be fixed by one isolated molecule with regularity.

Next, the types and abundances of the fixed target nucleic acid fragments 106 are found. The nucleic acid molecules 108 labeled with the fluorescence substances are reacted with the substrate, on which the target nucleic acid fragments 106. Then, the nucleic acid molecules 108 labeled with fluorescence are reacted with the substrate, on which the target nucleic acid fragments 106 have been fixed. Then the nucleic acid molecules labeled with fluorescence would contain the nucleic acid sequences complementary to the target nucleic acid fragments 106. Any of standard fluorochromes such as Cy3 and Cy5 or semiconductor particles made of Zn—Se, etc. may be used for the fluorescence substance labels. If there are many target nucleic acid fragments 106 to be labeled, fluorescent beads containing the fluorescence substances may be used for the fluorescence substance labels. For example, each of the contents of two types of fluorescence substances is set to ten levels and two types of fluorescence substances may be mixed with the levels of the contents thereof varied to prepare 100 types of fluorescence beads; assuming that three types of fluorescence substances be mixed, a set of 1000 discriminable beads may be easily prepared. For example, a set of 100 fluorescence beads, which are capable of being discriminated when two-wavelength laser beam (Luminex Corporation) is irradiated thereon, is commonly available. The surfaces of the fluorescence beads may be chemically modified and caused to be bound to the nucleic acid molecules to prepare the nucleic acid molecules 108 labeled with the fluorescence substances. After hybridization, appropriate non-specific absorbed substances are washed away and fluorescence is detected to analyze the target nucleic acid fragments 106. If the nucleic acid molecules 108 labeled with the fluorescence substances are labeled with only one standard fluorescence molecule, such as Cy3 and Cy5, one molecule of fluorescence would be observed at the positions on the substrate, where the target nucleic acid fragments 106. In this case, because of weak fluorescence, high-sensitivity fluorescence detector, e.g., EM-CCD, is needed for detection thereof. The use of fluorescence beads as the fluorescence substances induces the emission of fluorescence stronger than one molecule of fluorescence, making it possible to fluorescence to be satisfactorily detected even with a standard CCD. Since the bond pads 102 are formed on the support substrate 101 with regularity, e.g., they are formed into a lattice shape, the fluorescent spots may be observed at the positions with regularity on fluorescent images. For this reason, even though the nucleic acid molecules 108 labeled with the fluorescence substances become adherent non-specifically to the support substrate, they may be easily identified and removed from the luminescent spots of the fluorescence images. This advantage is practically very useful in analyzing a trace amount of samples and in observing weak fluorescence. To discriminate the types of the fluorescence substances or fluorescence beads, an emission spectrum is dispersed by diffraction grating and irradiated on the photosensitive surface of the CCD to determine the strengths of fluorescence in each of pixels divided in the wavelength. Alternatively, the types of the fluorescence substances or fluorescence beads may be discriminated based on the ratio between reflected light and transmitted light by a dichroic mirror with substantial wavelength-dependency as one of reflection characteristics. After the individual luminescent spots are discriminated, they may be summed up to obtain finally the types of the target nucleic acid fragments 106 and the number of luminescent spots, namely information on their abundances. For example, if the bond pads 102 are formed at the pitch of 1 μm, $10^6$ bond pads would exist in a 1 mm square; in this case, the number of each of given types of target nucleic acid fragments, among the total number of $10^6$ molecules, may be determined.

Hereinafter, giving an example of microRNAs as specific targets, the third embodiment is described in detail.

Assuming that microRNAs be targets, sequence data on individual microRNA molecules may be obtained from a known microRNA base sequence database (e.g., http://www.microrna.org/). Based on the obtained data, primers for reverse description may be designed. The lengths of the primer bases ranges preferably from 10 to 15 bases and a 10-base DNA is attached at the 5' terminal of each of the primer bases as a capture tag molecule 107. For example, 1000 types of primers may be designed and synthesized for human microRNAs. 1000 types of the synthesized primers are mixed in equal amount to prepare a primer cocktail; the primer cocktail for reverse transcription and the reverse transcriptase are mixed to obtain a total RNA; a reverse transcription reaction is induced under the temperature conditions of 37° C. to 40° C. to synthesize a cDNA, in order to cause the target nucleic acid fragments 106 and the capture tag molecules 107. Alternatively, to cause the capture tag molecules 107 to be bound to the target nucleic acid fragments 106, RNAs are used for the target nucleic acid fragments 106 and RNAs with about 10 bases in length are used for the capture tag molecules 107, and they are bound to each other in the presence of T4RNA ligase. On the substrate, complementary DNA strands to the 10-base nucleic acids, namely the capture molecules 107, are fixed one molecule at a time as the capture tag molecules 104. How to fixing the capture molecules 104 to the particles 103 one molecule at a time is described in a fourth embodiment in detail. cDNAs (formed by binding the target nucleic acid fragments 106 and the capture tag molecules 107) are hybridized on the substrate by means of a common practice to fix the target nucleic acid fragments 106 on the substrate.

In the same manner as above, the sequence data on the individual microRNAs is obtained from the known microRNA base sequence database and accordance with the same base sequences as those of this sequence, 1000 types of oligonucleotides with biotin modified at the 5' terminal thereof are synthesized.

Cy5, Cy5.5, or Cy3, for example, may be used for the fluorescence substances used as the fluorescence beads and they may be detected at two kinds of excitation lights, 532 nm and 633 nm. To prepare polystyrene beads at a given die mixture ratio, solutions of different ratios of concentration for each dye are prepared and mixed in the step of synthesizing polystyrene beads from styrene monomers. To modify the surfaces of the polystyrene beads with, e.g., avidin easily, copolymerization reaction between acrylic acid/methacrylic acid and styrene is used to introduce carboxyl groups on the surfaces of the beads in order to react with the amino groups of avidin in the presence of a cross-linker, carbodiimide.

The fluorescence beads modified with avidin may be reacted with the synthesized oligonucleotides with biotin modified at the 5' terminal thereof to the nucleic acid molecules 108 labeled with the fluorescence substances.

Next, the nucleic acid molecules 108 labeled with fluorescence substances are hybridized to the substrate 101 with the target nucleic acid fragments 106 fixed thereon in the common manner.

After washing away with a detergent solution containing sodium dodecyl sulfate, the fluorescence images are obtained to identify the correspondence between the individual fluorescence luminescent spots of each of the bond pads and the types of fluorescent beads, and the number of the luminescence spots are counted, achieving the analysis of the abundances of different types of microRNAs.

The number of detectable types of nucleic acids depends on the number of the discriminable fluorescent beads. Assuming that about 1000 types of microRNAs exist, 1000 types of fluorescence beads may be sufficient for the microRNAs; as described above, the contents of the fluorescence substances are set to 10 levels and they are mixed with the levels of the contents of three types of fluorescence substances varied to make a set of beads capable of discriminating 1000 types of microRNAs easily, enabling all types of microRNAs to be detected at a time. Moreover, to determine the emission level of a certain type of microRNAs, the nucleic acid molecules 108 labeled with the fluorescence substances corresponding to the certain type of microRNAs are prepared and the fluorescent beads are also prepared in the same quantity. In the case of the microRNAs other than the certain microRNAs, the same type of fluorescent beads are used for the microRNAs excluding the aforementioned microRNAs; this enables the abundances of all the microRNAs to be given as the countable numbers of values without preparing necessarily 1000 types of fluorescent beads and the abundance ratio of the certain microRNAs to total microRNAs to be found.

Alternatively, a method involving such steps is very useful in determining the expression level of only a certain nucleic acid molecule as: labeling the capture tag molecules 107, in advance, with a fluorescence dye with different emission wavelength or emission intensity different from those of the nucleic acid molecules 108 labeled with the fluorescence substances; and assuming that the number of fluorescence luminescent spots based on the fluorescence die labeled with the capture tag molecule 107 correspond to the number of all the sample nucleic acid molecule and the numbers of the fluorescence luminescent spots of the fluorescence substances labeling the nucleic acid molecules 108 labeled with different types of fluorescence substances correspond to the numbers of various types of sample nucleic acid molecules to determine the abundance ratios between the numbers of luminescent spots of both of them.

Moreover, the method of the present invention may be applicable to analyses of sample nucleic acids, as well as sample molecules, e.g., proteins, other than the sample nucleic acids by optimizing the capture molecules 104. For sample biomolecules composed of a plurality of types of biomolecules, the target biomolecules are fixed at the fixation positions with regularity on the support substrate 101 one at a time using, e.g., an appropriate antibody as capture molecules 104, and biomolecules, which are known to adsorb to specific biomolecules, for detection are reacted with the sample biomolecules fixed on the support substrate to detect the biomolecules for detection, making it possible to analyze them in the same manner as that of sample nucleic acids. Thus, the comprehensive and quantitative analysis of the types and abundances of the target biomolecules may be conveniently and rapidly performed at single-molecule sensitivity and resolution.

With respect to the aforementioned embodiment, the example, in which the target DNA samples are fixed on the substrate one by one to make it easy to count the molecules, is given; needless to say, fixing the target DNA samples on the substrate one at a time is not an essential requirement, and the object of the present invention, namely analysis of the types and abundances of the target DNA samples is fulfilled if the samples may be counted even though they are fixed by two or three.

Second Embodiment

Figure 2:
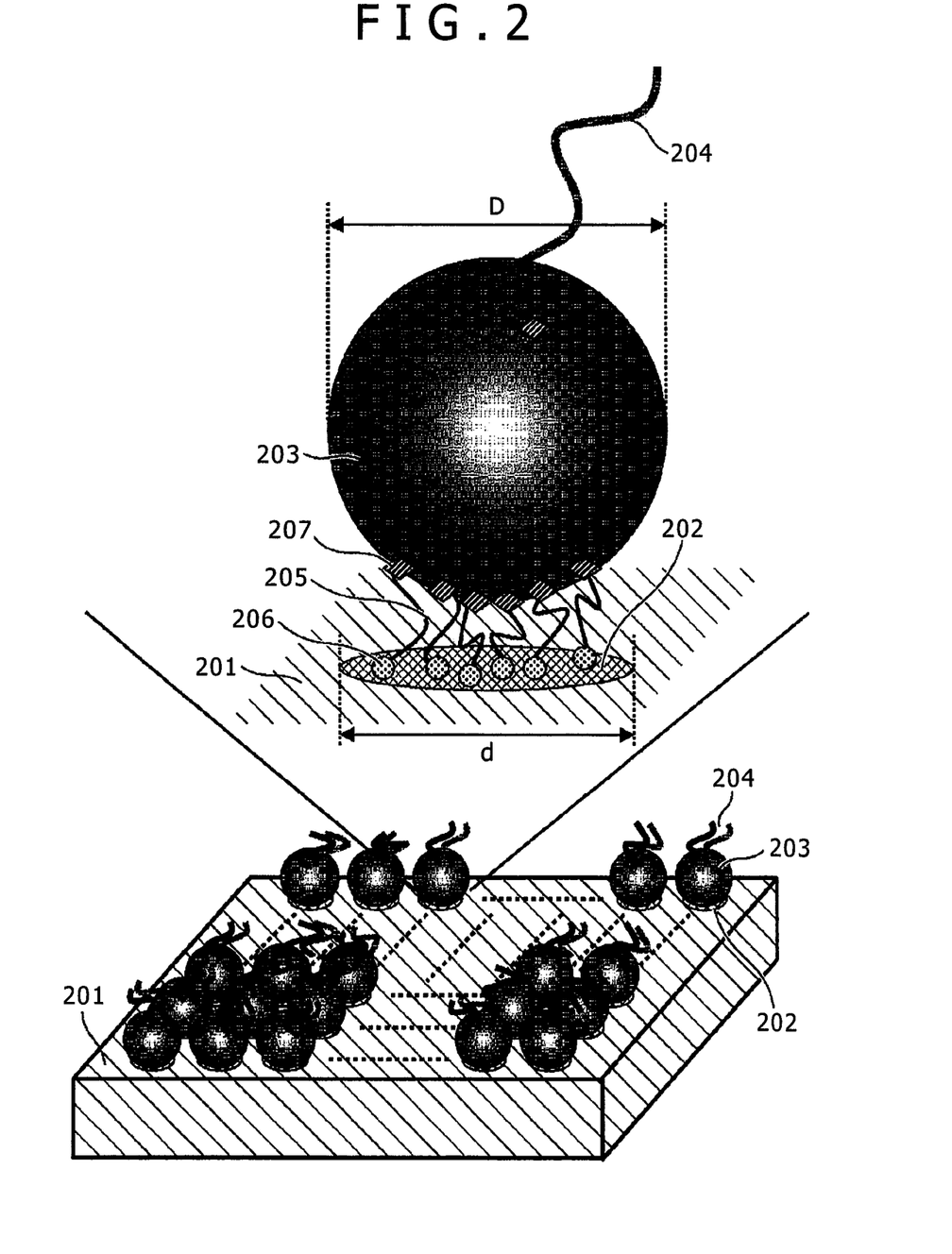
FIG. 2 is a view explaining an example of the configuration of a device used for the analysis method according to this embodiment.

The configuration of a device according to a second embodiment is described by reference to FIG. 2. Bond pads are formed into a lattice shape on a support substrate 201 with regularity, as shown in, for example FIG. 2. The bond pads 202 and particles 203 are bound to each other by means of chemical bond or chemical interaction through a linear molecule 205. It is preferable that the functional group at the terminal of a linear molecule 206 is linked to the bond pad 202 by means of chemical interaction. In this case, it is also preferable that the functional group interact weakly with the support substrate 201 and strongly with the bond pad 202. From this point of view, substrates made of quartz glass, sapphire, or silicon may be used for the support substrate 201. Alternatively, the bond pads 202 may be made of one selected from the materials of gold, titanium, nickel, and aluminum. A sulfhydryl group, amino group, carboxyl group, phosphate group, aldehyde group, or the like, for example, may be selected for a functional group 206 considering the combination of the support substrates 201 and the bond pads 202. The linear molecules 205 play a role in bridging between the particles 203 and the bond pads 202 and have no limitation on the length thereof; however, for low molecular weight of linear molecules 205, it is preferable to be linear molecules, each composed of about 3 to 20 carbon atoms. The functional group 207 at the 5' terminal of the linear molecule 205 brings an adherence property to the particle 203. When high molecular weight of linear molecules 205 are used, those, which have a plurality of side chains including both the side chains containing the functional group 206 and the side chains containing the functional group 207, may be used. Metal particles or semiconductor particles may be used for particles 203. For example, gold particle products of 5 to 100 nm in diameter are commercially available and may be immediately used. Moreover, semiconductor particle products, made of e.g., CdSe, of about 10 to 20 nm in diameter are commercially available and may be immediately used. The functional group, which may be used for the functional group 207, depends on the types of the particles; it is preferable that a sulfhydryl group or amino group is used for the gold particles. For the semiconductor particles, the product of particles, of which surfaces modified with streptavidin, are commercially available and biotin may be used for the functional group 207. Furthermore, the particles made of one of high-molecular weight of materials, such as polystyrene, may be used for the particles 203. The use of the high-molecular weight of materials enables the particle sizes of the particles to be uniformed and the particle sizes widely ranging from several tens nm to several μm may be selected. It is preferable in that the surfaces of the particles may be modified using a functional group contained in the high-molecular weight of material as a scaffolding to make uniform the amount of the functional groups to be introduced to induce fixation reaction for fixing the capture molecules 204 on the surfaces of the particles. In particular, it is preferable that excellent reproducibility would be achieved when only one capture molecule 204 is fixed on the surface of the particle 204.

For the capture molecules 204, single strand DNA or RNA nucleic acid molecules may be used. The terminal of the nucleic acid molecule is modified in advance in the same manner as that of the functional groups 207 to react with the particles 203. It is preferable to only one capture molecule 204 is fixed to a single particle 203, and one capture molecule 204 would be fixed on the bond pad 202.

To identify probes using a convenient technique for fluorescence detection, it is preferable that the probes are separated at the intervals of about 1 μm taking the diffraction limitation into account. For this reason, the size of the particles 203 is appropriately 1 μm or less.

To form the bond pads 202 on the support substrate 201, the thin film process, which has been already used practically in the semiconductor field, may be used. For example, after evaporation and sputtering through a mask or after thin film formation by means of evaporation and sputtering, the bond pads 202 may be formed by dry-etching or wet-etching. The use of the thin film process makes it easy to position the bond pads 202 with regularity. The intervals between the bond pads 202 may be arbitrarily set; when optical metrology is used for detection, the intervals are preferably set to at least 1 μm taking the diffraction limitation into account.

After the bond pads 202 are formed on the support substrate 201, the linear molecules 205, which couple between the particles 203 and the bond pads 202, are supplied to fix the linear molecules 205 on the bond pads 202. In this case, to prevent effectively the linear molecules 205 from non-specifically adsorbing on the support substrate 201, a material of high adhesive power on the support substrate 201 is reacted with the support substrate 201, and then the linear molecules are supplied. A silane coupling agent, for example, may be used for the material with high adhesive power. Next, the particles 203 with the capture molecules 204 fixed thereon are supplied on the substrate to fix the particles 203 on the bond pads 202, achieving the device for nucleic acid analysis.

When the particles 203 are fixed on the bond pads 202, a plurality of particles 203 may be occasionally fixed on one bond pad 202. If a plurality of particles 203 are fixed on one bond pad 202, information on different types of nucleic acid fragments are overlapped, making it impossible to analyze the nucleic acids correctly. For this reason, on one bond pad 202, only one particle 203 must be fixed. To address this problem, the inventors of the present invention conducted fixation experiments repeatedly under various conditions and earnestly made efforts; it was demonstrated that if the condition that the diameter d of the bond pad 202 is smaller than the diameter D of the particle 203 is held, only one particle 203 may be fixed on one bond pad 202. If the particle 203 of the size equal to or larger than the bond pad 202 is fixed on the bond pad 202, an unreacted linear molecule is shielded by the fixed particle 203, preventing it from reacting with another particle. Moreover, further earnest efforts made it clear that since electrostatic repulsion force exerts between the particles if the particles 203 have electric charges on the surfaces thereof, only one particle 203 is fixed on one bond pad 204 even through the diameter d of the bond pad 202 is larger than the diameter D of the particle 203. Accordingly, it is suggested that if the particle 203 has small electric charge on the surface thereof with weak electrostatic repulsion force, the diameter d of the bond pad 202 is preferably smaller than the diameter D of the particle 203, whereas if the particle 203 has large electric charge on the surface thereof with strong electrostatic repulsion force, the diameter d of the bond pad 202 may not be always smaller than the diameter D of the particle 203.

U.S. Pat. No. 6,859,570 discloses a method for detecting fluorescence by a bundle of optical fibers, which involves the steps of: forming a hole (minute recipient) on individual optical fibers, which are bundled together, at the end thereof; inserting the particle with an antibody attached to capture the target biomolecule; and detecting fluorescence at each hole by the optical fiber. In contrast, the present invention requires no hole (minute recipient) even though the particles are arranged into a lattice shape; rather, inserting the particle in the hole may cause problems, for example the washing step requires excess time. For this reason, with respect to the present invention, it is preferable, as described in the second embodiment, that the particle are arranged into the lattice shape on the support substrate using the bond pads.

Third Embodiment

Figure 3:
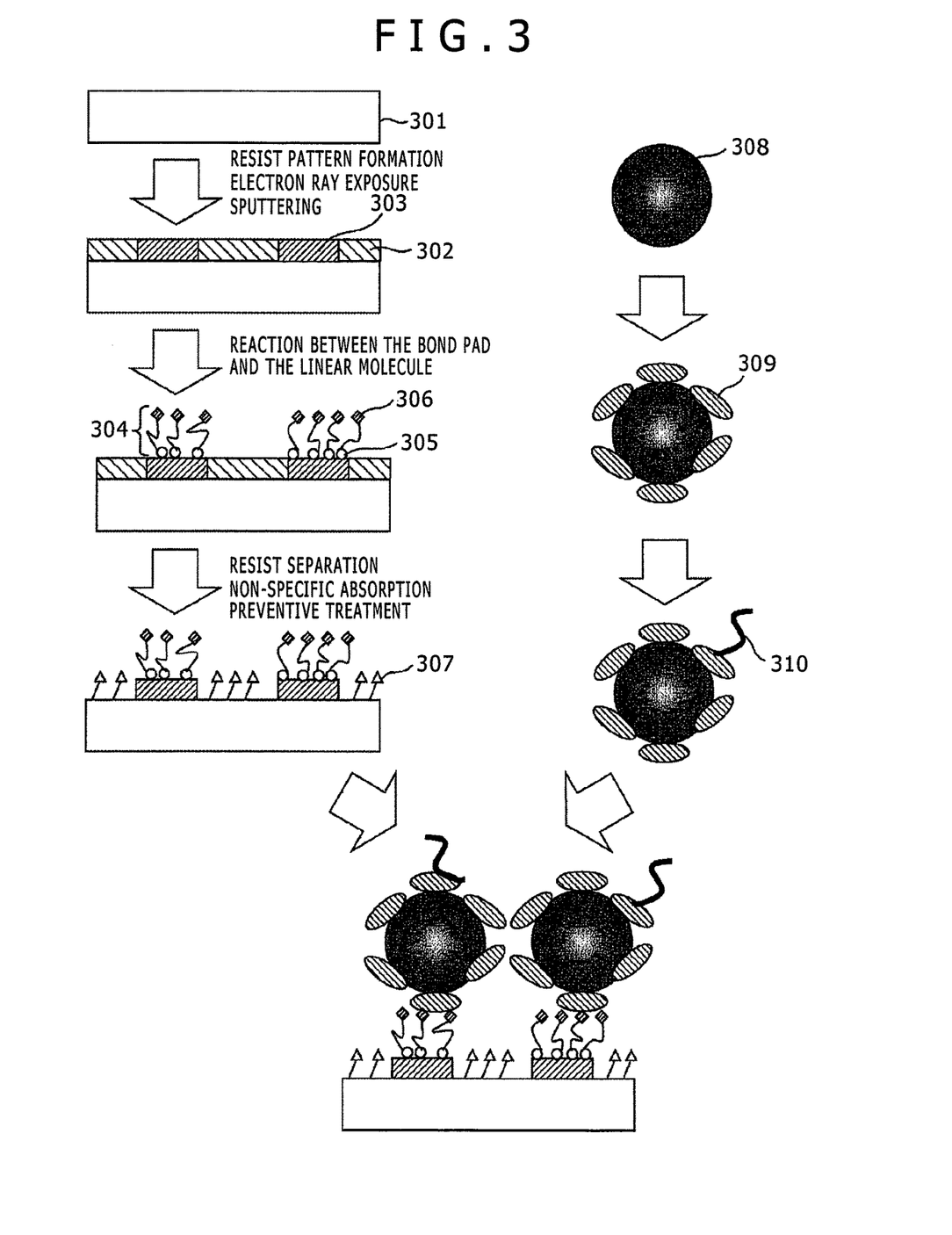
FIG. 3 is a view explaining an example of a method for manufacturing the device used for the analysis method according to this embodiment.

A method for fabricating the device according to the third embodiment is described by reference to FIG. 3. Positive photoresist 302 for electron ray is coated on a smooth support substrate 301 by the spin coating method. The substrates made of glass, sapphire, silicon wafer, or the like are used for the smooth support substrate. If excitation light need to be irradiated from the back side, which is the other side of the surface with the particles arranged, to fabricate the device, a quartz substrate or sapphire substrate, both of which have excellent light transmissibility, may be used. Positive photoresist includes polymethylmethacrylate and ZEP-520A (ZEON Corporation, Japan). Alignment is performed based on the marker positions on the substrate and electron ray lithography exposure is applied to form through-holes in the photoresist. The through-holes of 15 nm in diameter, for example, are formed. Depending on the number of nucleic acid molecules to be analyzed by parallel processing, it is suitable to form the through-holes at the intervals of about 1 μm taking into account manufacturing convenience, high yield, and the number of nucleic acid molecules to be analyzed by parallel processing. Depending on the number of nucleic acid molecules to be analyzed by parallel processing, the area for forming the through-holes is determined largely by the precision and resolution of positions detected by a detector. When reaction sites (bond pads) are formed, for example, at the intervals of μm, one million reaction sites may be formed assuming that the area for forming the through-holes is 1 mm×1 mm. After through-hole formation, the material, of which the bond pads 303 are formed, e.g., gold, titanium, nickel, aluminum, or the like is formed into a film by sputtering. If the substrate made of glass or sapphire are used for the smooth support substrate and gold, aluminum, or nicked is used for the material for the bond pads, it is preferable to insert a titanium or chrome fin film between the substrate material and the bond pad material. Next, linear molecules 304 are reacted with the bond pads 303. If the bond pads 303 are made of gold, titanium, aluminum, and nickel, it is preferable to use a sulfohydnyl group, a phosphate group, and a thiazole group, respectively for functional groups 305 at the terminals of the linear molecules. Biotin, for example, may be used for a functional group 306 on the other side of the linear molecule. The linear molecules are reacted with the bond pads and then the resist is separated. After resist separation, non-specific absorption preventive treatment is applied on the surface of the remaining region on the support substrate excluding the area, in which the bond pads are formed. To achieve prevention of absorption to nucleotides labeled with a fluorescence dye, the surface of the support substrate is coated with non-specific absorption preventive molecules 307 containing functional groups negatively charged. For example, epoxysilane is coated on the surface by the spin coating method, heat-treated, treated with a weak acid solution (about pH 5 to 6) to open the rings of epoxy groups and introduce OH groups onto the surface, achieving non-specific absorption preventive effects.

It is preferable to modify the surfaces of particles 308 with avidin 309 in advance. When gold or platinum particles are used, the surface is react with aminothiol, then with biotin-succinimide (NHS-Biotin, Pierce), and finally with streptavidin to modify the surface with avidin easily. When the particles of metal other than gold or platinum are used, the surface is heat-treated in the presence of oxygen to oxidatively treat the surface, and the surface is reacted with aminosilane, then with biotin-succinimide (NHS-Biotin, Pierce) and finally with streptavidin. This makes it easy to modify the surfaces of the metal particles with avidin. When semiconductor particles are used for the particles, commercially available particles may be used. For example, the particles of 15 to 20 nm in diameter, of which product name is "Qdot (R) Streptavidin Label" (Invitrogen), may be used. Alternatively, polystyrene beads may be used for the particles. For example, the particles of 40 nm in diameter, of which product name is "FluoSphere® NeutrAvidin® Modification" (Invitrogen), may be used. When oligonucleotides are used for the capture molecules 310, the terminals thereof are modified with biotin for synthesis, making it easy to fix the oligonucleotides on the particle 308. The particles 308 with the capture molecules 310 fixed thereon are fixed on the bond pads 303, making it possible to fabricate the device for nucleic acid analysis according to the third embodiment.

Fourth Embodiment

Figure 4:
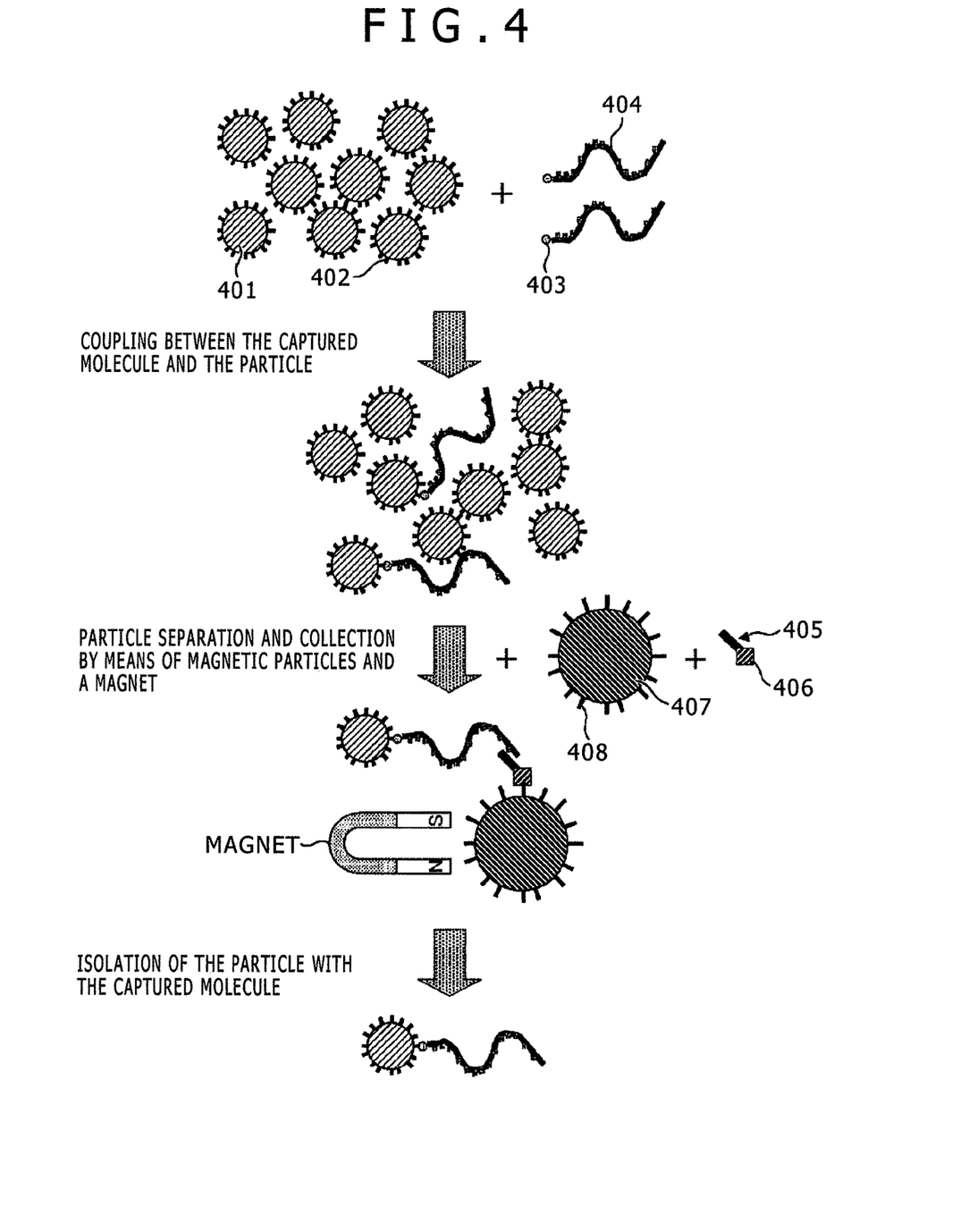
FIG. 4 is a view of an example of a method for preparing particles fixed to their corresponding single molecules according to this embodiment.

In the fourth embodiment, an example of a method for manufacturing the particles with single capture molecules fixed thereon, especially a method for fixing only one capture molecule to one particle is described by reference to FIG. 4. Binding sites 402 for capturing capture particles 404 are bound on the surfaces of the particles 401. For example, streptavidin may be used for the binding sites and commercially available streptavidin-coated particles (Invitrogen) may be used for the particles. The capture molecules 404 are modified with the binding sites 403 in advance. The particles, which are easy to bind to the binding sites 403 on the surfaces of the particles 401, are selected for the binding sites 402. For example, when the aforementioned streptavidin is used for the binding sites 402, biotin is used for the binding sites 403. The oligonucleotides, of which terminals are modified with the binding sites 403, are synthesized, making it possible to synthesize easily the capture molecules 404 with the binding sites 403 at the terminals thereof. Next, the particles 401 are reacted with the capture molecules 404 to bind the capture molecules 404 to the particles 401. To fix only one capture molecule 404 to one particle of the capture molecule 404, it is preferable to the number of molecules for the capture molecules 404 in unit volume is smaller than the number of the particles 401. If the capture molecules 404 more than the particles 401 exist, more than one capture molecule is likely to fix to one particle 401. The study by inventers showed that when with the number of the particles 401 ten times the number of the capture molecules 404, they are reacted, no capture molecule 404 was captured on about 90% of the particles 401 and only one capture molecule 404 was captured on about 9% of the particles 401. This result well corresponds to the result predicted when Poisson distribution is assumed. Accordingly, if only the particles 401 with the capture molecule 404 captured are collected, more than 90% of the collected particles 401 would be the particles 401, each of which has captured one capture molecule 404. For example, the capture molecules 404 are bound to magnetic particles 407, making it possible to collect the particles by means of a magnet. Oligonucleotides 405, which have the complementary sequence to the terminal sequence of the capture molecule 404 and have the terminal modified with the binding site 406, are prepared, and the surfaces of the magnetic particles 407 are coated with biding sites 408, which bind to binding sites 406, in advance. The magnetic particles 407 manufactured in this way may be used to separate and collect the particles 401, each of which has captured one capture molecule 404, at high rate, at least 90%. To isolate the particles 401 from the magnetic particle 407, for example, denature treatment (high-temperature treatment), which separates the double strand of the capture molecules 404 and the nucleotides 405, may be used. The isolated particles 401 may be fixed at the given positions on the support substrate using the method described in the second embodiment and the device for analyzing the nucleic acid, which has fixed only one capture molecule 404 according to the fourth embodiment, may be fabricated.

Moreover, to increase the ratio of the particles, each of which has captured only one molecule, the use of electrophoresis is effective. Specifically, taking use of such a characteristic that depending on the number of the nucleic acid molecules captured on the particles, electric charge varies on the particles, the particles with the nucleic acid molecules captured are electrophoresed in gel, e.g., agarose, to separate electrophoretic patterns according to differences in the electric charge, namely the number of captured nucleic acid molecules. The particles with no nucleic acid particle captured migrate over the shortest distance and the particles with only one nucleic acid molecule captured form a band at the secondarily shortest distance. Accordingly, this band is cut off, making it possible to obtain the particles, each of which has captured only one nucleic acid molecule, at high purity.

Fifth Embodiment

Figure 5:
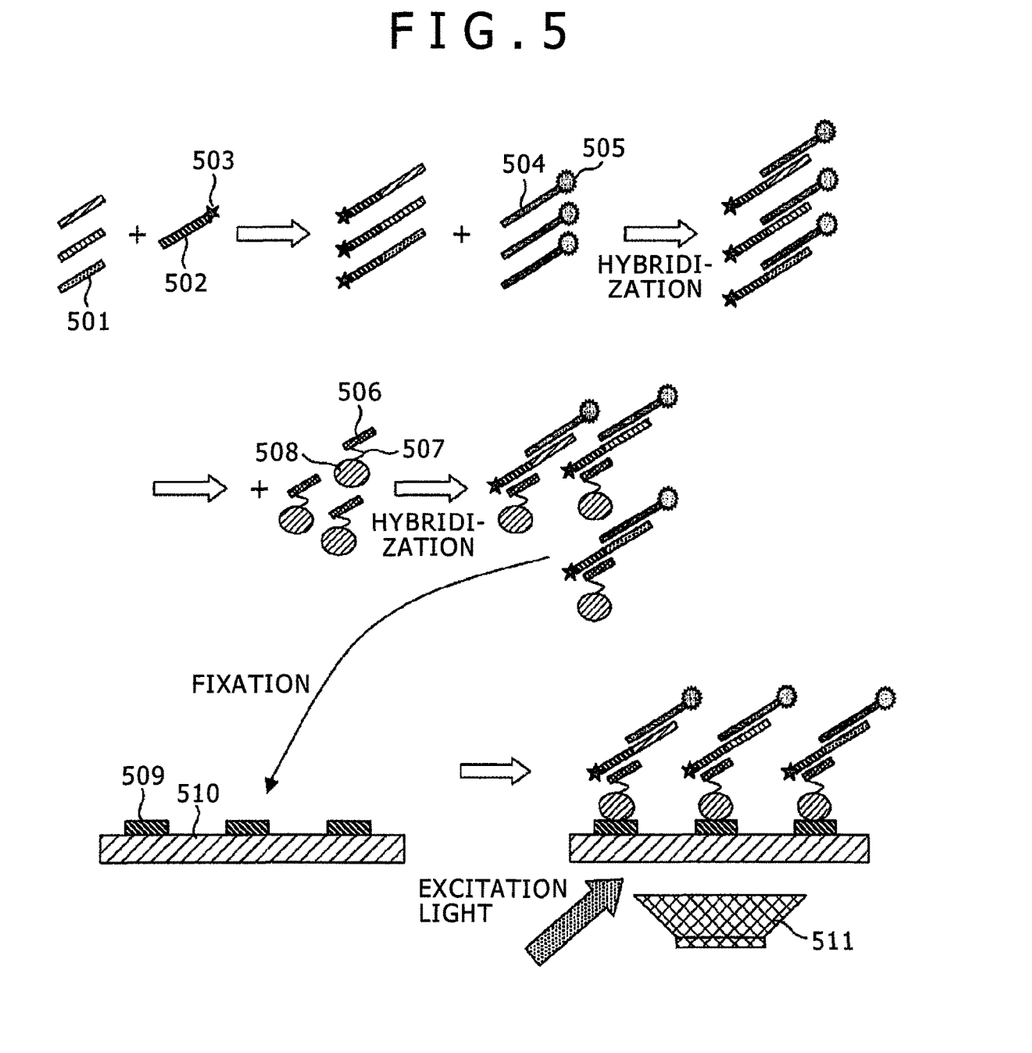
FIG. 5 is a view explaining an example of the analysis method according to this embodiment.

The configuration and analytical method of a device according to the fifth embodiment is described by reference to FIG. 5. Capture tag molecules 502 labeled with a fluorescence die 503 are bound to target nucleic acid fragments 501. To bind them, ligation reaction or coupling reaction between functional groups, which involves the step of introducing a functional group, e.g., an amino group or succinimide group, into the target nucleic acid fragments 501 and the capture tag molecules 502 in advance. In particular, when the target nucleic acid fragments 501 are microRNAs, the use of T4RNA ligase is effective assuming that RNA molecules of about 10 to 20 base length are the capture tag molecules 502. The capture tag molecules 502 labeled with the fluorescence dye 503 are bound to the target nucleic acid fragments 501, and hybridized with the nucleic acid molecules 504 labeled with a fluorescence substance 505. Since the nucleic acid molecules 504 are used to identify the individual target nucleic acid fragments, they need to have base sequences representative of individual gene sequences. To design the sequences, the melting temperature, which provides the indicator of stability of the nucleic acid double strand, need to be within a certain temperature range with respect to the individual labeled molecules. The range is preferably narrow and more preferably within a given temperature of ±3° C. Moreover, the homology between the base sequences of the labeled molecules is preferably low, and the highest homology is preferably 70% or lower and more preferably 60% or lower. Next, using the method described in the fourth embodiment, the particles 508, each of which has fixed to only one capture molecule 506 through a binding molecule 507, are prepared in advance, and the prepared particles 508 are added for hybridization, making it possible to prepared one pair of molecules obtained hybridization between the target nucleic acid fragments 501 and the nucleic acid molecules 504 labeled with the fluorescence substance 505 on particles 508. As described in the first embodiment, fluorescence beads containing fluorescence substances may be used for the fluorescence substances 505.

Next, the particles 508, on which the hybrid has been formed, are fixed on bond pads 509 formed on a support substrate 510. The conditions described in the first embodiment are applicable as fixation reaction conditions. Finally, fluorescence of the fluorescence dye 503 and the fluorescence substances 505 are measured by a detector 511 and the numbers of luminescent spots of the fluorescence dye 503 and for each of the types of the fluorescence substances 505 are calculated. The number of luminescent spots of the fluorescence dye 503 corresponds to the total number of the target nucleic acid fragments 501 and the number of luminescent spots of each of the types of the fluorescence substances 505 corresponds to the number of each of the types of the target nucleic acid fragments. Accordingly, the ratio between these numbers, making it possible to calculate the ratio of the number of each of the types of nucleic acid fragments to the total number of the target nucleic acid fragments. Calculating this ratio is effective especially in conducting expression comparative analysis among samples. For example, to search for a marker gene, which is difference in expression level between healthy subjects and patients with a specific disease, it is required that a gene, of which expression level is equal between both samples, is found and the expression level is standardized; however, it is practically very difficult to find the gene, of which expression level is equal between both the samples. In particular, the Non-patent Literature 5 indicates that quantitative PCR has a major problem. In contrast, since the method according to the fifth embodiment enables the ratio of the number of each of the types of individual sample molecules to the total number of sample molecules to be easily calculated, the healthy subjects may be compared directly to the patients by means of the ratio to number of all the samples. This advantage is useful especially in conducting comparative analysis of nucleic acid molecules on clinical specimens.

Sixth Embodiment

Figure 6:
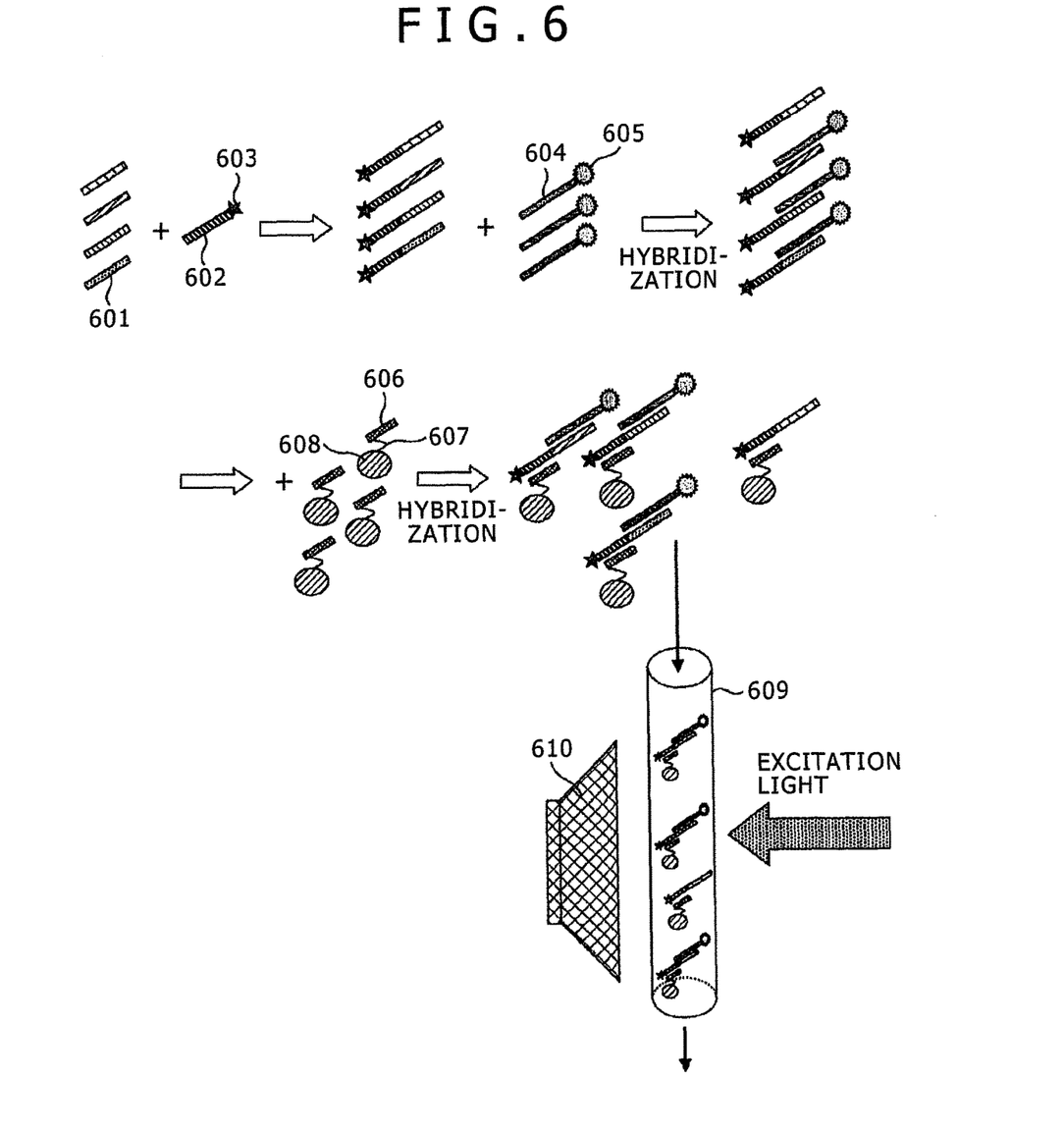
FIG. 6 is a view explaining an example of the analysis method according to this embodiment.

An analytical method according to the sixth embodiment is described by reference to FIG. 6. Capture tag molecules 602 labeled with a fluorescence dye 603 are bound to target nucleic acid fragments 601. To bind them, ligation reaction or coupling reaction between functional groups, which involves the step of introducing a functional group, e.g., an amino group or succinimide group, into the target nucleic acid fragments 601 and the capture tag molecules 602 in advance. In particular, when the target nucleic acid fragments 601 are microRNAs, the use of T4RNA ligase is effective assuming that RNA molecules of 10 to 20 base length are the capture tag molecules 602. The capture tag molecules 602 labeled with the fluorescence dye 603 are bound to the target nucleic acid fragments 601, and hybridized with the nucleic acid molecules 604 labeled with a fluorescence substance 605. Since the nucleic acid molecules 604 are used to identify the individual target nucleic acid fragments, they need to have base sequences representative of individual gene sequences. To design the sequences, the melting temperature, which provides the indicator of stability of the nucleic acid double strand, need to be within a certain temperature range with respect to the individual labeled molecules. The range is preferably narrow and more preferably within a given temperature of ±3° C. Moreover, the homology between the base sequences of the labeled molecules is preferably low, and the highest homology is preferably 70% or lower and more preferably 60% or lower. Next, using the method described in the fourth embodiment, the particles 608, each of which has fixed to only one capture molecule 606 through a binding molecule 607, are prepared in advance, and the prepared particles 608 are added for hybridization, making it possible to prepared one pair of molecules obtained hybridization between the target nucleic acid fragments 601 and the nucleic acid molecules 604 labeled with the fluorescence substance 605 on particles 608. As described in the first embodiment, fluorescence beads containing fluorescence substances may be used for the fluorescence substances 605.

Next, the particles 608, on which hybrid has been formed, are poured into a fluid channel 609 and excitation light is irradiated on them to measure the intensities of fluorescence of the fluorescence dye 603 and the fluorescence substances 605 using a detector 610. It is preferable to set the diameter of the fluid channel 609 to less than two times the diameter of the particles 608, making it possible to identify the individual particles 608 to measure fluorescence without measuring the fluorescence of a plurality of fluorescence dyes 603 at a time. The number of fluorescence luminescent spots of the fluorescence dye 603 is counted to obtain the value equivalent to the total number of nucleic acid fragments. On the other hand, only when the fluorescence of the fluorescence dye 603 and the fluorescence of the fluorescence substances 605 are measured at a time, the luminescent spots for a specific fluorescence substance are counted to obtain the value equivalent to the number of each of the types of the nucleic acid fragments. The ratio between both the numbers is calculated, making it possible to calculate the ratio of number of molecules for each of the types of sample molecules to the total number of sample molecules. The method according to the sixth embodiment enables the expression levels for individual genes to be obtained as the ratio to the expression level of all the genes; direct comparison between different samples, e.g., healthy and patient samples may be conducted. This advantage is effective, especially in conducting comparative analysis of the nucleic acid molecules on clinical specimens. Moreover, the scattering light from the particles 608 is detected and combined with fluorescence measurement, improving the accuracy of identification.

Herein, giving an example of a circular fluid channel as the fluid channel 609, the analytical method has been described; the use of a flat thin planar fluid channel for the fluid channel 609 makes it possible to detect two-dimensionally the fluorescence of the fluorescence dyes 603 and fluorescence of the fluorescence substances 605, as well as the scattering light from the particles 608, improving the detection speed and sensitivity.

For the particles 608, the particles made of a polymer, e.g., polystyrene, or the magnetic particles, which have been manufactured using a polymer containing magnetic metal powder, may be used. In particular, it is preferable that when the magnetic particles are used, before the reacted particles 608 are poured into the fluid channel 609, the capture tag molecules 602 labeled with the fluorescence dye 603 and nucleic acid molecules 604 labeled with the fluorescence substances 605, both of which are not fixed on the particles 608 remaining in the reaction solution and are unreacted, may be easily removed; and only when the fluorescence of the fluorescence dye 603 and the fluorescence of the fluorescence substances 605 are measured at a time, measurement is made easy to count the luminescent spots of a specific fluorescence substance, which provides a major merit.

Seventh Embodiment

Figure 7:
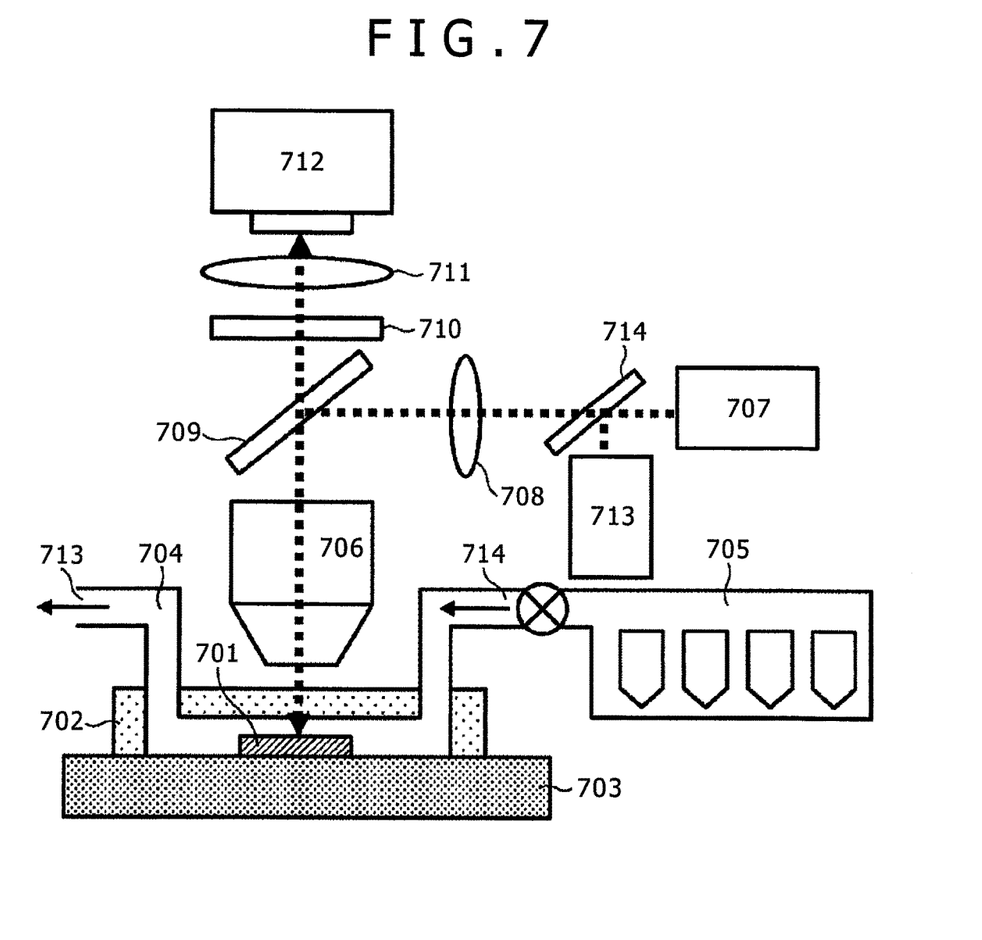
FIG. 7 is a view explaining an example of an apparatus of nucleic acids according to this embodiment.

In the seventh embodiment, an example of the preferable configuration of an apparatus for nucleic acid analysis using the device for nucleic acid analysis is described by reference to FIG. 7.

The apparatus for nucleic acid analysis according to the seventh embodiment has a part for supplying a target nucleic acid sample solution, a solution of molecules labeled with fluorescence, and a detergent solution to the substrate of the device for nucleic acid analysis; a part for regulating the temperature to conduct hybridization on the substrate of the device for nucleic acid analysis; a pert for irradiating light on the substrate of the device for nucleic acid analysis; and a part for detecting emission light to measure the fluorescence of fluorescence substances, which are the molecules labeled with fluorescence. More specifically, the substrate 701 of the device for nucleic acid analysis is put on a temperature regulating plate 703, and a fluid channel formation member 702, on which a fluid channel 70 has been formed, is bonded on the plate to form a reaction chamber. For the fluid channel formation member 702, PDMS (Polydimethylsiloxane), for example, may be used.

To an inlet, a solution feeding unit 705 is connected to supply a target nucleic acid sample solution, a solution of the molecules labeled with fluorescence, and a detergent solution, all of which are contained in the solution feeding unit 705 sequentially to the substrate of the device 701 for nucleic acid analysis. After the target nucleic acid sample solution and the solution of the molecules labeled with fluorescence are sent to the substrate 701 of the device for nucleic acid analysis, the solutions are retained on the substrate 701 of the device for nucleic acid analysis in the fluid channel 704, the temperature of the reaction solution on the substrate 701 of the device for nucleic acid analysis controlled within the range from 30° C. to 80° C. on the temperature plate 703 to conduct hybridization, After hybridization, the detergent solution is supplied to the substance 701 of the device for nucleic acid analysis from the solution feeding unit 705 to wash away unreacted substances.

After washing, fluorescence is detected. Depending on the types of fluorescence substances to be used, an appropriate excitation light source may be selected. For example, when Cy5, Cy5.5, and Cy3 are used for the fluorescence substances as fluorescence beads, two kinds of excitation lights, 532 nm (YAG laser) and 633 nm (He—Ne laser) may be used. The laser lights emitted from the YAG laser source (wavelength of 532 nm, output of 20 mW) and the He—Ne laser source (wavelength of 633 nm, output of 20 mW) are regulated by means of a dichroic mirror 714 so that the two laser lights proceed coaxially and guided to an objective lens 706 by the dichroic mirror, and irradiated on the substrate 701 of the device for nucleic acid analysis. The fluorescence emitted from the molecules labeled with fluorescence proceeds reversely in a coaxial optical path with the excitation light, is collected on the objective lens 706, passes through the dichroic mirror 709, and is formed into an image on the light-sensitive surface of a two-dimensional CCD camera 712 by an imaging lens 711. The scattering light of the excitation light is removed through an optical filter 710.

As described above, assembling the solution feeding unit, the temperature regulating plate, the excitation light source, and fluorescence detection unit to build the apparatus for nucleic acid analysis, makes it possible to conduct automatically nucleic acid analysis by hybridization, improving considerably the throughputs of conventional techniques.

LIST OF REFERENCE SIGNS 101, 201, 510 support substrate
102, 202, 303, 509 bond pad
103, 203, 308, 401, 508, 608 particle
104, 204, 310, 404, 506, 606 capture molecule
105, 507, 607 binding molecule
106, 501, 601 target nucleic acid fragment
107, 502, 602 capture tag molecule
108 nucleic acid molecule labeled with fluorescent substance
205, 304 linear molecule
206, 207 functional group
301 smooth support substrate
302 positive photoresist for electron beam
305, 306 functional group at the terminal of the linear molecule
307 non-specific absorption preventive molecule
309 avidin
402, 403, 406, 408 binding site
405 oligonucleotide
407 magnetic particle
503, 603 fluorescence dye
504, 604 nucleic acid molecule
505, 605 fluorescence substance
511, 610 detector
609, 704 fluid channel
701 substrate of the device for nucleic acid analysis
702 fluid channel formation member
703 temperature regulating plate
705 solution feeding unit
706 objective lens
707 YAG laser light source
708 lens
709, 714 dichroic mirror
710 optical filter
711 imaging lens
712 two-dimensional CCD camera
713 He—Ne laser light source

The invention claimed is:

1. A method for nucleic acid analysis comprising:
preparing a plurality of separate particles on a support substrate;
fixing individual target nucleic acid fragments, of a group of different types of target nucleic acid fragments, on single ones of the particles in a one-to-one correspondence on the support substrate; and
hybridizing a plurality of different nucleic acid molecules, which have different known base sequences and have been labeled with different fluorescent substances, with the group of the target nucleic acid fragments on the support substrate; and
detecting the different fluorescent substances labeling the hybridized nucleic acid molecules;
counting one or more luminescent spots corresponding to individual ones of the fluorescent substances for each of the different hybridized nucleic acid molecules; and
calculating a ratio of the one or more luminescent spots for each of the different hybridized nucleic acid molecules to a total number of luminescent spots for all of the different hybridized nucleic acid molecules to evaluate an abundance thereof for each type of the target nucleic acid fragments,
wherein the fixing of the individual target nucleic acid fragments and the hybridizing of the nucleic acid molecules are non-polymerase chain reaction (non-PCR) processes.

2. The method for nucleic acid analysis according to claim 1,
wherein the particles are magnetic beads,
wherein the different fluorescence substances are particles containing several types of fluorescence substances with compounding ratios different for each of the types of the target nucleic acid fragments,
wherein unhybridized nucleic acid molecules labeled with the fluorescence substances are separated from the magnetic beads after the hybridization step, and
wherein the fluorescence substances labeling the nucleic acid molecules hybridized with the target nucleic acid fragments on the magnetic particles are detected after separation from the unhybridized nucleic acid molecules.

3. The method for nucleic acid analysis according to claim 1, further comprising:
labeling the group of the target nucleic acid fragments with a first fluorescent substance,
wherein the nucleic acid molecules that are hybridized with the group of target nucleic acid fragments are labeled with the fluorescent substances different from the first fluorescent substance, and wherein a plurality of ratios of number of luminescent spots of the first fluorescent substance and the one or more luminescent spots of the respective fluorescent substances which label the nucleic acid molecules are calculated to evaluate an abundance thereof for each of the types of the target nucleic acid fragments.

* * * * *